United States Patent [19]

Monzer

[11] Patent Number: 4,560,277

[45] Date of Patent: Dec. 24, 1985

[54] PROCESS AND DEVICE FOR QUALITATIVE AND QUANTITATIVE MEASUREMENT OF IRREGULARITIES AND IMPURITIES ON AND IN TRANSPARENT OR SEMITRANSPARENT FLEXIBLE SHEET MATERIALS

[75] Inventor: Helmut Monzer, Wiesbaden, Fed. Rep. of Germany

[73] Assignee: Hoechst Aktiengesellschaft, Frankfurt am Main, Fed. Rep. of Germany

[21] Appl. No.: 493,758

[22] Filed: May 11, 1983

[30] Foreign Application Priority Data

May 17, 1982 [DE] Fed. Rep. of Germany ....... 3218571

[51] Int. Cl.$^4$ .............................................. G01B 9/02
[52] U.S. Cl. ..................... 356/357; 356/73; 356/359; 356/366
[58] Field of Search ............... 356/73, 357, 359, 360, 356/364, 366, 367

[56] References Cited

U.S. PATENT DOCUMENTS 3,359,852 12/1967 Wilczynski et al. ............... 356/359
4,367,951 1/1983 Hammon ............................ 356/357

FOREIGN PATENT DOCUMENTS 0032710 7/1981 European Pat. Off. .
1920928 11/1969 Fed. Rep. of Germany .

Primary Examiner—Davis L. Willis
Assistant Examiner—Matthew W. Koren
Attorney, Agent, or Firm—Schwartz, Jeffery, Schwaab, Mack, Blumenthal & Evans

[57] ABSTRACT

Disclosed is a process for the qualitative and quantitative measurement of irregularities and impurities on and in transparent or semitransparent flexible sheet materials, comprising the steps of producing interference fringes by obliquely directing a light beam onto the surface of a sheet to be examined to produce two partial beams; placing the sheet to be examined on a reflecting reference surface and forming the partial beams by reflection from this reference surface and from the surface to be examined; superposing the two partial beams, whereby an interference field is obtained which is equivalent to the surface profile of the sheething to be examined; evaluating the interference field to determine the extension of the surface profile; additionally irradiating the sheet by a polarized light beam; passing the polarized light beam through a second polarizer; and evaluating the polarized light beam after passing through the second polarizer. Also disclosed is an apparatus for carrying out this process.

24 Claims, 6 Drawing Figures

PROCESS AND DEVICE FOR QUALITATIVE AND QUANTITATIVE MEASUREMENT OF IRREGULARITIES AND IMPURITIES ON AND IN TRANSPARENT OR SEMITRANSPARENT FLEXIBLE SHEET MATERIALS

BACKGROUND OF THE INVENTION

The present invention relates to a process for the qualitative and quantitative measurement of irregularities and impurities on and in transparent or semitransparent flexible sheet materials, in particular, film webs. The invention also pertains to a device for carrying out the process.

In the process, interference rings are produced by means of a light beam directed at the surface of the sheet, part of the light beam being reflected from the surface of the sheet and part of it being reflected from another surface after passing through the sheet. The two partial beams are superposed again and fed to a recording device. Apart from this process, polarization effects are created in the sheet by means of a penetrating polarized light beam, which is also fed to a recording device.

Flexible materials, in particular in the form of polymer films, are used in many technical fields for a great number of different purposes. For some applications, such as, e.g., magnetic tape films or capacitor films, it is necessary to subject the surface of the base film to continuous quality control tests. In cases where very thin films are coated, for example, with magnetic coatings to give audiotapes or videotapes, or where films of this type are used for producing roll-type capacitors, it is indispensible to know the surface quality in order to obtain usable end products.

For example, it is known in magnetic tape production to control the surface quality before and after coating, since variations in the distance between the magnetic head and the surface of the magnetic tape affect both the recording quality and the voltage level read. As a consequence, therefore, the surface quality must be continuously controlled.

One frequently employed control method is the use of an interference microscope, where the enlarged image of the surface to be examined is superposed by interference phenomena. The interference phenomena in the form of interference rings or fringes are created by splitting the light beams of a monochromatic light source into two partial bundles of beams, by surface reflection and diffraction or reflection from a mirror, and superposing these partial bundles of beams again. As a result, parallel interference lines having a distance of half a wavelength appear in the microscope. In the case of sodium light, this distance is 0.29 μm. If irregularities are present on the surface to be controlled, deflection of the interference lines occurs, whereby the height of these irregularities can be determined with the aid of the line distance or the number of intereference rings surrounding the irregularities.

When examining the surfaces of magnetic tapes, it has been found that the irregularities, i.e., elevations or indentations, have diameters which rarely exceed 25 μm, and in some cases are even less than 2 μm. In most cases, they have the shape of points, arches or cones. In order to be able to successfully employ this known process for determining the surface quality, highly magnifying microscopes (in general 250-power or 500-power) must be used, which means that the area which can be examined is not larger than 0.01 mm$^2$ to 0.05 mm$^2$. This is not adequate, however, for an appropriate and reliable control of the surface quality.

German Offenlegungsschrift No. 19 20 928 discloses a device for examining the evenness and smoothness of surfaces by means of interference measurement, whereby the surface to be examined is exposed to light and then inspected obliquely through a planar surface of glass or the like which is adjacent, but not in direct contact with the surface to be inspected, the angles of exposure and inspection being chosen such that no total reflection is caused.

European Patent Application No. 00 32 710 is concerned with a process and device for analysis of the surface properties of flexible materials, in particular of film webs, by producing interference fringes by means of a light beam directed obliquely onto the surface to be examined, whereby a portion of the light beam is reflected from another surface, and the two partial beams are superposed again. The object to be examined is put on a reflecting reference surface and the partial beams are formed by reflection from the reference surface and the surface to be examined so that an interference field is obtained which is equivalent to the surface of the object to be measured, i.e., which shows the differences as compared with the profile of the reference surface. This interference field is then evaluated in a known manner to determine the extension of the surface profile in the horizontal and vertical directions, with the aid of the distances between the interference lines and the wavelength of the irradiated light.

Although the two last mentioned processes bring about essential improvements in the process described initially, they nevertheless still have a serious disadvantage. Thus, it is possible to determine the number and height of superficial irregularities using these methods, but it is not possible to distinguish between irregularities which are due to particles (for example, dust) adhering to the surface, and irregularities which are due to particles embedded between the surfaces (for example, blisters or specks).

Such a differentiation is, however, of crucial importance for a manufacturer of flexible sheet materials which are, e.g., to be used as audio or videotapes or as capacitor films. Only if the process operator knows the exact nature of the irregularities, can he decide whether it will be necessary to change the process conditions in respect of avoiding abrasion, electric charging during the film transport (attraction of dust particles), etc., whether the formulation of the raw materials or the manufacturing conditions will have to be changed or whether, for example, other filters and service lives of the filters will have to be chosen.

SUMMARY OF THE INVENTION

It is therefore an object of the present invention to develop a process by which it is possible, with the use of an interference measuring method, to determine both the number and height of the adhering and embedded irregularities and to distinguish clearly between outer impurities (outer cleanliness) and inner, i.e., embedded impurities (inner cleanliness).

Another object of the invention resides in the provision of an apparatus for carrying out this process.

In accomplishing these objects, there has been provided in accordance with the present invention a process for the qualitative and quantitative measurement of irregularities and impurities on and in transparent or semitransparent flexible sheet materials, comprising the steps of producing interference fringes by obliquely directing a light beam onto the surface of a sheet to be examined, whereby one portion of the light beam is reflected from the surface to be examined, whereas another portion of the light beam is reflected from another surface to produce two partial beams; placing the sheet to be examined on a reflecting reference surface and forming the partial beams by reflection from this reference surface and from the surface to be examined; superposing the two partial beams, whereby an interference field is obtained which is equivalent to the surface profile of the sheet to be examined; evaluating the interference field to determine the extension of the surface profile in the horizontal and vertical directions with the aid of the distances between the interference fringes and the wavelength of the irradiated light; additionally irradiating the sheet by a polarized light beam; after passing through the sheet, passing the polarized light beam through a second polarizer; and evaluating the polarized light beam after passing through the second polarizer.

In accordance with another aspect of the invention, there has been provided a device for carrying out this process.

Further objects, features and advantages of the present invention will become apparent from the detailed description of preferred embodiments which follows, when considered together with the attached figures of drawings.

BRIEF DESCRIPTION OF THE DRAWINGS

With reference to the attached drawings, the invention will be explained in greater detail. It is understood, however, that the embodiments shown therein are in no sense limiting.

In the drawings

DETAILED DESCRIPTION OF PREFERRED EMBODIMENTS

Figure 1:
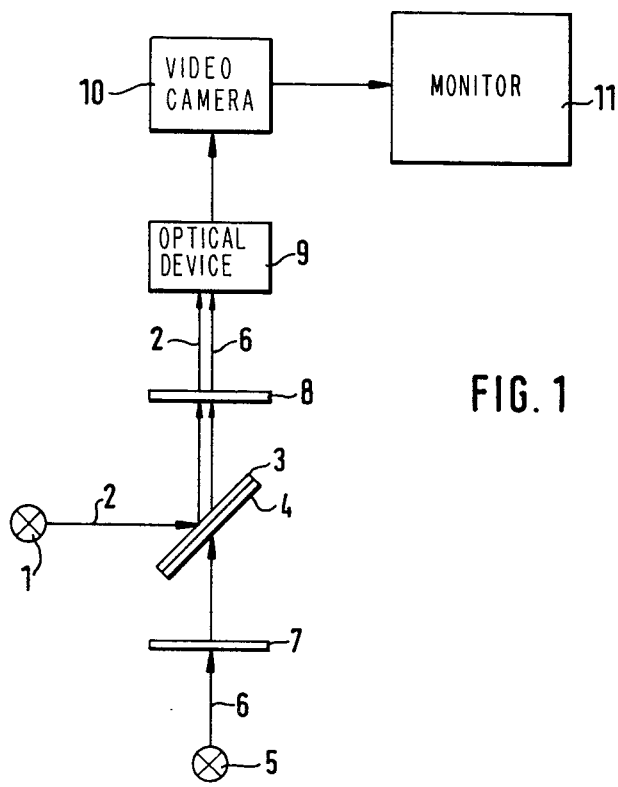
FIG. 1 is a schematic view of an appropriate device in accordance with the invention.

A process for the qualitative and quantitative measurement of irregularities and impurities on and in transparent or semitransparent flexible sheet materials, in particular film webs, is carried out by producing interference fringes by means of a light beam directed obliquely onto the surface to be examined, whereby one portion of the light beam is reflected from the surface to be examined, whereas another portion of the light beam is reflected from another surface, and the two partial beams are superposed again, whereby the sheet to be examined is put on a reflecting reference surface and the partial beams are formed by reflection from this reference surface and from the surface to be examined, so that an interference field is obtained which is equivalent to the surface profile of the sheet to be examined, i.e., which is different from the profile of the reference surface. This interference field is then evaluated in a manner known per se, to determine the extension of the surface profile in the horizontal and vertical directions with the aid of the distances between the interference fringes and the wavelength of the irradiated light. The process is characterized in that the flexible sheet to be examined is additionally irradiated by a light beam which, before and after passing through the sheet, passes through a polarizer and, after passing through the last polarizer, is evaluated in a known manner.

By means of the process of this invention it has for the first time become possible to make both qualitative and quantitative statements on the number and size of the impurities adhering to and being embedded between the surfaces of flexible sheets. It is now possible to clearly distinguish between adhering dust particles and blisters or specks embedded in the surfaces. The process according to the invention enables manufacturers of films to carefully monitor and adjust the manufacturing process and/or to select specific polymers.

Irradiation of the flexible sheet materials can be carried out from below or from above. In the latter case, the portion of reflected light is recorded. The angle of irradiation depends on the position and arrangement of the recording device(s).

The light beam producing the interference phenomena and the polarizing light beam can be recorded by two different recording devices, but it is particularly advantageous to direct the two beams to the same recording device.

It has proved to be especially advantageous to provide possibilities for eliminating either the light beam producing the interference rings or the polarized light beam. By doing so, the interference rings and the polarization effects can be represented separately and they can be more clearly distinguished, since accumulations and interactions are avoided. In the simplest case, elimination is effected either by switching off one of the two light sources, by arranging an eliminating mechanism in the path of the light beam producing the interference fringes or by pivoting or rotating one of the two polarizers away from the incident polarized light beam.

In the simplest case, the object to be examined, i.e., the flexible sheet, is fixed on the reference surface, but if larger surfaces are to be examined, it is advantageous to move the sheet over the surface, either by steps or continually. For this purpose, conventional advancing appliances, for example, rollers, are generally used. Care has to be taken that no air is enclosed between the reference surface and the sheet. A close contact to the reference surface can, for example, be achieved by roller pressure, by the application of gas by means of an air knife or by producing a vacuum.

These measures are well known in the art and need not be discussed in detail within the framework of this invention. In the simplest case, the recording device(s) is (are) high-power magnifier(s); however, microscopes are preferred because of the higher resolution of the interference fringes and the polarization effects. The observed effects are classified, measured by means of graduations and evaluated by calculation.

Other recording devices are cameras by which images of the occurring effects are recorded. These pictures can be evaluated subsequently or can be used as a comparison with the visual impression.

A particularly preferred process arrangement comprises a combination of visual observation by means of a microscope, recording by means of a video camera and representation on a monitor.

This invention also comprises a device for carrying out the process. In a simple embodiment, schematically illustrated in FIG. 1, it is comprised of a light source 1, which generates the light beams 2 producing the interference fringes. A surface 4 is arranged at an angle relative to the light source 1, on which the sheet 3 is placed in close contact. An optical device 9 is provided by which the produced interference fringes are made visible. The device is characterized in that a further light source 5 is provided for the generation of a polarized light 6 and in that one polarizer 7, 8 is arranged before and after the sheet. In a preferred embodiment, the device is designed such that one of the two light sources can be switched off or so that at least one of the two polarizers can be eliminated, so that the effects can be observed separately.

Eliminating one of the polarizers is effected by pivoting or rotating it away from the polarized light beam, using known devices.

The surface 4 can be made of a transparent or semitransparent material, for example, a thick glass or plastic plate, which is cambered in order to facilitate the application and transport of the sheet material, whereby the flexible sheet is tightly pressed against the convex side thereof. For the pressing-on of the sheet material, known means, such as tension rolls or springs, are employed. The surface 4 may also be comprised of a second layer of the flexible sheet if care is taken that no air is enclosed between the layers. Air enclosures are removed by means of the devices mentioned in the description of the process.

An optical device 9, such as a microscope is provided to record the interference patterns produced by the optical system described above. Preferably, the apparatus also includes a video camera 10 and a monitor 11, so that the process operator can continuously monitor the test results.

Figure 2:
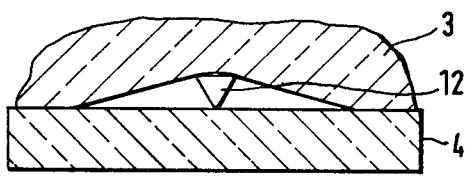
FIG. 2 is a schematic cross-sectional view of a particle anchored in the surface of the flexible sheet.
Figure 3:
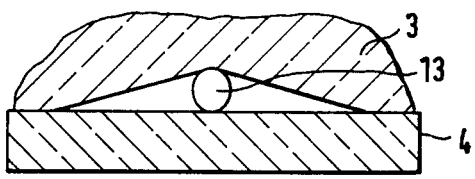
FIG. 3 is a schematic cross-sectional view of a dust particle lying on the surface of the flexible sheet.
Figure 4:
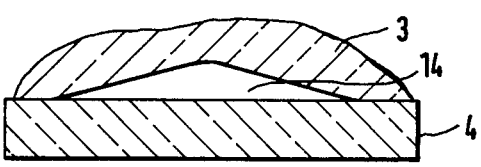
FIG. 4 is a schematic cross-sectional view of a blister embedded in the surface of the flexible sheet.

FIGS. 2, 3 and 4 illustrate the types of defects which can be evaluated according to the present invention. FIG. 2 illustrates a particle 12 anchored within the flexible sheet. FIG. 3 shows a dust particle lying between the surfaces of the sheets 3 and 4, and FIG. 4 shows a blister 14 embedded between the surfaces of the sheets 3 and 4.

Figure 5:
FIG. 5 is an interference photograph of a flexible sheet, showing interference fringes having a light center (blister) and interference fringes having a dark center (dust or embedded particles)

In FIG. 5 there is seen an interference photograph of a flexible sheet which shows that it is possible to distinguish between interference fringes which have a light center (blister) and interference fringes having a dark center (dust or embedded particles).

Figure 6:
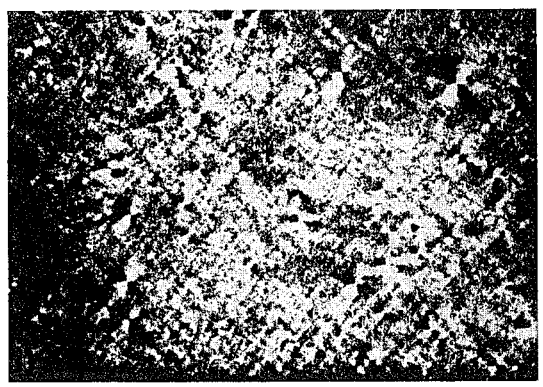
FIG. 6 is a polarization photograph of another flexible sheet, showing particles with a polarization effect (anchored particles) and particles without a polarization effect (dust).

FIG. 6 is a polarization photograph of a flexible sheet which demonstrates that it is possible to distinguish between particles having a polarization effect (anchored particles) and particles having no polarization effect (dust particles).

What is claimed is:

1. A process for the qualitative and quantitative measurement of irregularities and impurities on and in a transparent or semitransparent flexible materials in the form of a sheet, comprising the steps of:
    placing the sheet on a reflecting reference surface;
    producing interference fringes by obliquely directing a light beam onto the surface of the sheet, whereby one portion of the light beam is reflected from the surface to be examined, whereas another portion of the light beam is reflected from the reference surface to produce two partial beams;
    superposing the two partial beams, whereby an interference field is obtained which is equivalent to the surface profile of the sheet;
    evaluating the interference field to determine the extension of the surface profile in the horizontal and vertical directions with the aid of the distances between the interference fringes and the wavelength of the irradiated light;
    passing a polarized light beam through the sheet;
    passing the polarized light beam which has passed through the sheet through a second polarizer; and
    evaluating the polarized light beam which has passed through the second polarizer.

2. A process as claimed in claim 1, wherein both the light beam producing the interference fringes and the polarized light beam are directed to the same recording device.

3. A process as claimed in claim 1, further comprising the step of selectively eliminating either the light beam producing the interference field or the polarized light beam.

4. A process as claimed in claim 1, wherein the sheet is moved by steps relative to the light beams.

5. A process as claimed in claim 1, wherein at least one of the light beams is directed to a microscope.

6. A process as claimed in claim 1, wherein at least one of the light beams is directed to a camera.

7. A process as claimed in claim 1, wherein at least one of the light beams is directed to a video camera.

8. A process as claimed in claim 7, further comprising the step of displaying an image of at least one light beam on a monitor.

9. A process as claimed in claim 1, wherein the sheet is moved continually relative to the light beams.

10. A device for the qualitative and quantitative measurement of irregularities and impurities on and in transparent or semitransparent flexible sheet materials, comprising:
    means, including a first light source, for producing interference fringes by oliquely directing a light beam from said first light source onto the surface of a sheet to be examined, whereby one portion of the light beam is reflected from the surface to be examined, whereas another portion of the light beam is reflected from another surface to produce two partial beams;
    means for superposing the two partial beams, whereby an interference field is obtained which is equivalent to the surface profile of the sheet to be examined;
    means, including an optical device, for evaluating the interference field to determine the extension of the surface profile in the horizontal and vertical directions with the aid of the distances between the interference fringes and the wavelength of irradiated light;
    means, including a second light source and a first polarizer for additionally irradiating the sheet by a polarizer light beam;
    a second polarizer positioned in the path of said polarized light beam after it passes through the sheet; and means, including an optical device, for evaluating the polarized light beam after passing through the second polarizer.

11. A device as claimed in claim 10, further comprising means for selectively eliminating one of the two light sources.

12. A device as claimed in claim 11, wherein said elimination means comprises means for rotating or pivoting at least one of the two polarizers.

13. A device as claimed in claim 10, further comprising means for selectively eliminating one of the two polarizers.

14. A device as claimed in claim 10, including a reflecting reference surface on which to place the sheet to be examined and means for moving the flexible sheeting relative to or simultaneously with the reference surface.

15. A device as claimed in claim 14, wherein the reference surface comprises a transparent plastic material.

16. A device as claimed in claim 14, wherein the reference surface comprises another layer of the flexible sheet material.

17. A device as claimed in claim 14, wherein the reference surface is cambered and the device comprises means for tightly pressing the flexible sheet material against the convex side thereof.

18. A device as claimed in claim 14, wherein the reference surface comprises a semitransparent plastic material.

19. A device as claimed in claim 14, wherein the reference surface comprises glass.

20. A device as claimed in claim 10, wherein the optical device comprises a microscope.

21. A device as claimed in claim 10, wherein the optical device comprises a camera.

22. A device as claimed in claim 21, wherein the camera is a videocamera.

23. A device as claimed in claim 22, further comprising a monitor for receiving a signal from said camera.

24. A device as claimed in claim 9, wherein the optical device comprises a microscope followed by a camera.

* * * * *